United States Patent [19]

Cumes et al.

[11] Patent Number: 4,880,408

[45] Date of Patent: Nov. 14, 1989

[54] MEDICAL IRRIGATION DEVICE

[76] Inventors: David M. Cumes, 4147 Marina Dr., Santa Barbara, Calif. 93110; Terence C. Honikman, 927 N. Kellogg Ave., Santa Barbara, Calif. 93111

[21] Appl. No.: 189,220

[22] Filed: May 2, 1988

[51] Int. Cl.[4] .............................................. A61M 5/18
[52] U.S. Cl. ........................................ 604/36; 604/37
[58] Field of Search .................. 604/36, 37, 153, 185, 604/212, 217

[56] References Cited

U.S. PATENT DOCUMENTS

| | | | |
|---|---|---|---|
| 1,015,895 | 1/1912 | Kelley | 604/37 |
| 1,925,230 | 9/1938 | Buckhout | 604/37 |
| 3,892,226 | 7/1975 | Rosen | 604/37 |
| 4,676,777 | 6/1987 | Watts | 604/37 |

Primary Examiner—Jerome L. Kruter
Attorney, Agent, or Firm—Christie, Parker & Hale

[57] ABSTRACT

A medical irrigation device which enables the introduction of a sterile fluid ito a urinary bladder and thereafter the withdrawal of the fluid containing particulate matter such as prestatic tissue, blood clots and stones is provided. The device enables the reintroduction into the bladder of the withdrawn fluid relatively free of particulate matter.

10 Claims, 2 Drawing Sheets

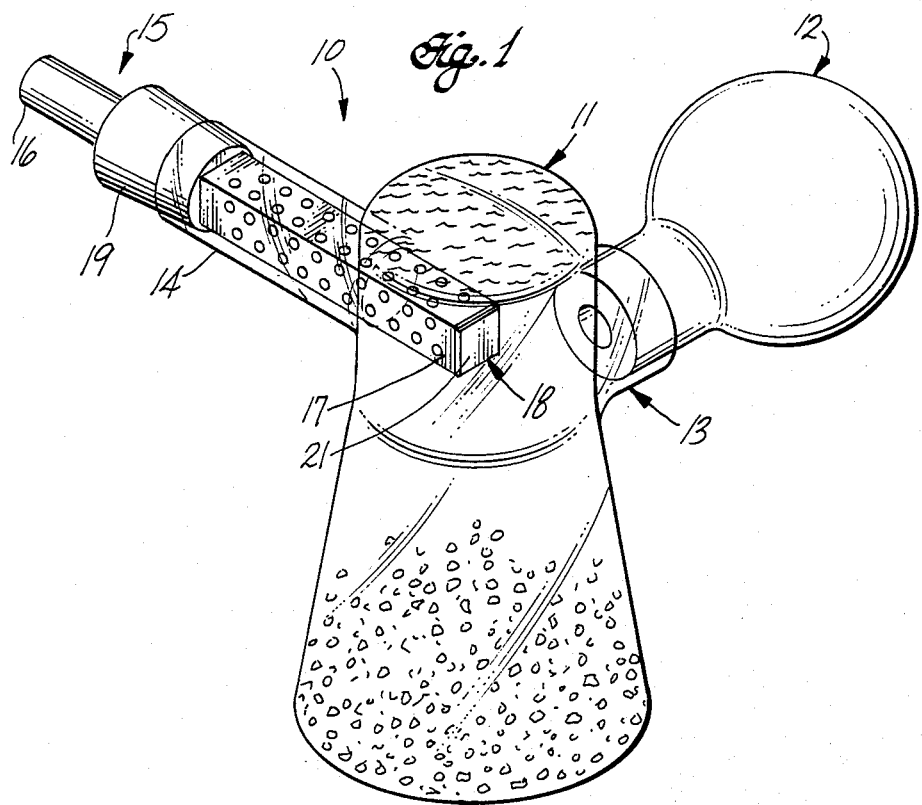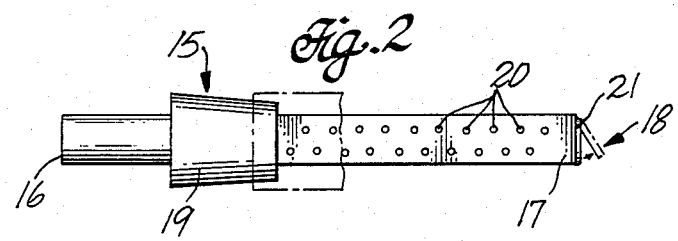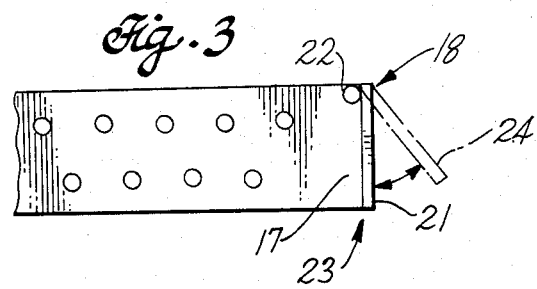

MEDICAL IRRIGATION DEVICE

FIELD OF THE INVENTION

The present invention relates to an irrigation device for use in medical procedures, particularly, irrigation of the urinary bladder following urological procedures.

BACKGROUND OF THE INVENTION

Following many urological procedures, it is often necessary to regularly irrigate the urinary bladder to flush out blood clots, stones, pieces of tissue and the like. This is generally achieved by introducing a sterile liquid into the bladder, withdrawing the liquid containing the material to be removed, and repeating the process a number of times.

At present, the most commonly used device for bladder irrigation is the Ellik evacuator. The Ellik evacuator comprises a pair of integrally formed chambers disposed in vertical alignment and having a restricted, central passageway in open communication between the two chambers. The upper chamber is provided with two ports, one of which is adapted for connection to a manually compressible bulb, the other of which is adapted for connection to a resectoscope for insertion into the urinary bladder.

In use the Ellik evacuator is completely filled with a sterile irrigation fluid and the resectoscope catheter passed into the bladder. Upon compression of the bulb, the sterile liquid is forced into the bladder, and is withdrawn following release of the bulb. Tissue and other particulate matter in the withdrawn fluid, which have a specific gravity greater than that of the sterile liquid, will tend to settle through the opening between the two chambers into the lower chamber. However, compression of the bulb produces eddy currents in the fluid in the upper chamber. These eddy currents tend to cause a portion of the particulate matter to remain in suspension, with the result, that tissue and other particulate matter are reinjected into the bladder each time the bulb is compressed after the initial compression. This is particulary is particularly the case when small prostatic chips or frond-like segments of a papillary bladder tumor are present, as they tend to float in the upper chamber and do not settle into the lower chambers.

A number of other disadvantages are encountered in using the Ellik evacuator, including the difficulty encountered in filling the Ellik evacuator and removing all the trapped air. This is particularly tedious as the filling procedure has to be repeated a number of times depending on the bulk of tissue that is resected. Each time the Ellik evacuator is emptied and refilled, the tissue that has been collected is separated from the Ellik evacuator. This requires the additional step of collecting the discarded tissue from drapes or irrigant basin later.

The Ellik evacuator is also an inefficient system, especially if a large bulk of tissue is resected. The large bulk of tissue tends to fill the lower chamber, thereby increasing the rate of flushing chips back into the bladder. The alternative is to empty and refill the Ellik evacuator more frequently. Even a partially filled lower chamber can result in this difficulty because irrigation vortices are created. The vortices tend to lift those chips that have already settled into the lower chamber back into the upper chamber, from where they are easily flushed back into the bladder.

The Ellik evacuator also creates a feeling of insecurity, since the surgeon must suspect that some chips remain in the bladder. The only way to correct this problem is to continue to empty and refill the Ellik evacuator until it remains clear through the final irrigation.

U.S. Pat. No. 3,892,226 is directed toward a urological irrigation-evacuator which seeks to overcome some of the difficulties encountered with the Ellik evacuator. This device comprises a fluid receptive manually compressible bulb and a specimen collecting receptacle. In fluid connection with the collecting receptacle is a first conduit means which is adapted to be connected to a resectoscope. In parallel array to the first conduit means is a second conduit means which is in fluid contact with the compressible bulb. There are two one-way valve means which provide fluid contact between the first and second conduit means; one providing contact between the upper portions of the conduits, and the other providing contact between the lower portions of the conduits.

In operation, the device of U.S. Pat. No. 3,892,226 is filled with sterile liquid and connected to a resectoscope which is passed into the urinary bladder. Upon compression of the bulb, liquid is forced from the second conduit, through the one-way valve connecting the upper portions of the conduits, into the first conduit, and from there into the bladder via the resectoscope. Release of the bulb generates negative pressure resulting in withdrawal of the liquid from the bladder into the first conduit means. Tissue and other particulate particles in the fluid withdrawn from the bladder, which have a specific gravity greater than that of the liquid, tend to settle or gravitate toward the specimen collecting receptacle. At the same time liquid is drawn from the first conduit means into the second conduit means through the one-way valve connecting the lower portion of the conduits. The tissue and other particulate matter is prevented from entering the second conduit means by means of a sieve which is positioned over the one-way valve connecting the lower portions of the conduit means.

Following the withdrawal of the fluid from the urinary bladder, the bulb is compressed once again and the process repeated.

While the device disclosed in U.S. Pat. No. 3,892,226 overcomes some of the problems encountered with the Ellik evacuator, it still relies on sedimentation of t he particulate matter drawn into the first conduit. Compression of the bulb will result in eddy currents being produced in the first conduit tending to cause the particulate matter to remain in suspension causing their reintroduction into the bladder.

SUMMARY OF THE INVENTION

The present invention comprises a medical irrigation device comprising a reservoir and a double-acting manually operable pump means. The reservoir has an inlet/outlet port through which fluid may be displaced outwardly and withdrawn inwardly by action of the pump means. The irrigation device is provided with an elongate hollow member which extends through the inlet/outlet port. The elongate hollow member has an open first end, positioned externally of the reservoir, adapted for connection to a catheter or resectoscope, and an open second end positioned within the reservoir The second end is provided with a one-way valve means which allows fluid to pass into the reservoir. The hollow elongate member further includes a plurality of pores in the walls of a portion of the hollow elongate member, with this portion being positioned within the reservoir. Each of the pores has a cross-sectional area substantially smaller than the cross-sectional area of the open second end of the elongate hollow member.

The double-acting manually operable pump means may be provided by the reservoir itself being compressible, or by a compressible moiety connected to the reservoir. At present it is preferred that the manually operable pump means is a rubber bulb connected to the reservoir. It is preferred that the rubber bulb is releasably connected to the reservoir by way of a port defined by a short outwardly extending hollow projection.

It is preferred that the inlet/outlet port is defined by an outwardly extending hollow projection. The elongate hollow member is then positioned so as to extend through the projection with the first end outside the projection and the second end either within the receptacle or the hollow projection, preferably within the receptacle. It is particularly preferred that the hollow elongate member is provided with a rubber bung which releasably secures the elongate member in the hollow projection.

The device of the present invention provides a number of advantages over irrigation devices of the prior art. These advantages include:

1. the device is filled only once;
2. the device has a non-return valve which prevents the return of any chips to the bladder—there is no reliance on sedimentation;
3. the device is easy to fill;
4. the device is capable of accommodating all the tissue from even the largest of prostates; and
5. the device is relatively simple and inexpensive to produce.

BRIEF DESCRIPTION OF THE DRAWINGS

These and other features and advantages of the present invention will be better understood by reference to the following detailed description when considered in conjunction with the accompanying drawings wherein:

FIG. 1 is a perspective view of an embodiment of the irrigation device of the present invention;

FIG. 2 is a fragmentary view, partly in section, showing the elongate hollow member 15 in greater detail;

FIG. 3 is a fragmentary view showing the one-way valve means 18 in greater detail.

DETAILED DESCRIPTION

Figure 4:
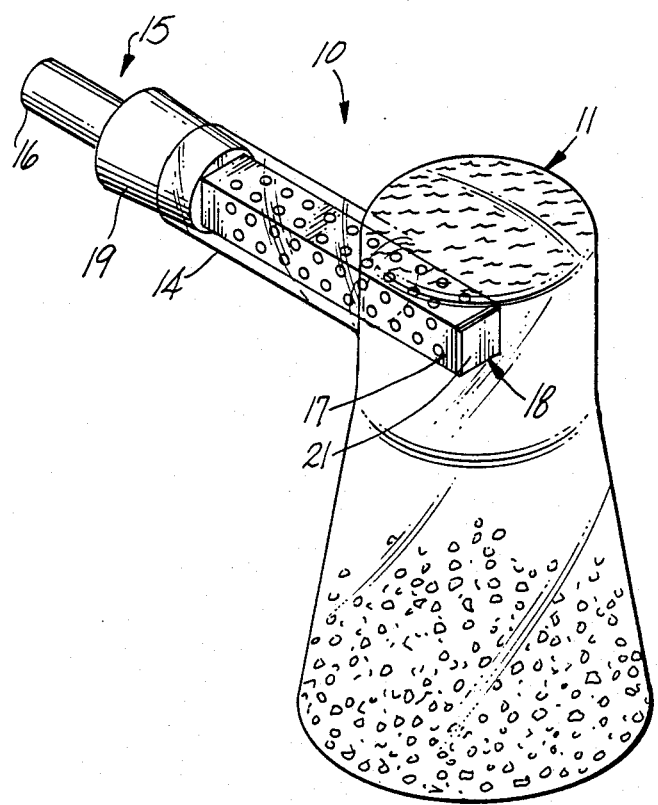
FIG. 4 is a perspective view of another embodiment of the irrigation device of the present invention.

Referring to FIG. 1 the medical irrigation device 10 includes a reservoir 11 and a compressible bulb 12 connected to the reservoir 11 by way of a short, outwardly extending hollow projection 13. The reservoir 11 includes an inlet/outlet port defined by an outwardly extending hollow projection 14. Positioned within, and extending through the outwardly extending hollow projection 14, is a hollow elongate member designated 15.

The hollow elongate member 15 has an open first end 16 positioned externally of the outwardly extending hollow projection 14 and reservoir 11. The first end 16 of the hollow elongate member 15 is adapted for connection to a resectoscope (not shown).

The hollow elongate member 15 has an open second end 17 positioned within the reservoir 11. The second end 17 is provided with a one-way valve means 18 such as gravity assisted, surge driven flapper valve. Positioned on the elongate hollow member 15 between the first end 16 and the second end 17 is a rubber bung 19. The rubber bung 19 acts to releasably secure the hollow elongate member 15 within the outwardly extending hollow elongate projection 14.

As is best shown in FIG. 2, the elongate hollow member 15 is provided with a plurality of pores 20 between the second end 17 and the rubber bung 19. The cross-sectional area of each of the pores 20 is substantially smaller than that of the second end 17.

In the embodiment of the present invention shown, the one-way valve means 18 comprises a flap 21 connected along one edge to the hollow elongate member 15 by means of the hinge 22. The hinge 22 enables the flap 21 to swing from a closed position 23 covering the second end 17 of the hollow elongate member 15 to an open position 24 in which the flap is away from the second end 17.

In use, the irrigation device 10 of the present invention is filled with a sterile liquid. Upon compression of the compressible bulb 12, the sterile fluid is forced from the reservoir 11 into the hollow elongate member 15 through the pores 20, the flow of liquid causing the closure of the one-way valve means 18 positioned in the second end 17 of the hollow elongate member 15. The sterile fluid flows through a first end of the hollow elongate member 15, through a resectoscope (not shown) connected to the first end 16, and into the urinary bladder of the patient.

Upon release of the compressible bulb 12, a pressure gradient is generated within the reservoir 11 and the sterile liquid, now containing particulate matter, is withdrawn from the bladder via the resectoscope. The withdrawn fluid passes into the hollow elongate member 15 through the first end 16. The flow of withdrawn fluid along the hollow elongate member 15 causes the flap 21 of the one-way valve means 18 to swing away from the second end 17. The second end 17 being open allows the passage of the withdrawn fluid and the particulate material therein into the reservoir 11 through the second end 17. Due to the cross-sectional area of the second end 17 large particles, such as stones and blood clots, present in the withdrawn fluid are able to pass into the reservoir 11.

Upon recompression of the bulb 12, liquid is once again forced from the reservoir into the hollow elongate member 15, and from there into the bladder via the resectoscope connected to the first end 16. As the flow causes the closure of the one-way valve means 18 positioned in the second end 17 of the hollow elongate member 15, liquid enters the hollow elongate member 15 only through pores 20. Due to the cross-sectional area of the pores 20 being substantially smaller than the cross-sectional area of the second end 17, large particles which entered the reservoir through the second end 17 are prevented from being reintroduced into the bladder as they are unable to pass through the pores 20. Accordingly, only liquid relatively free of particulate matter is introduced into the bladder following recompression of the bulb 12.

As is shown in FIG. 4, the medical irrigation device 10 need not be provided with a separate compressible moiety. In such an embodiment the reservoir 11 is compressible. Compression and release of the reservoir 11 leads to the functioning of the device 10 as previously described.

While the present invention has been described with particular reference to the one-way valve means 18 comprising a flap 21 connected by hinge 22 to the hollow elongate member 15, it will be appreciated by persons skilled in the art that other forms of one-way valves could be included in place of the particular one-way valve described.

As opposed to the portion of the hollow elongate member 15 between the rubber bung 19 and the second end 17 being provided with a plurality of pores 20, it is envisaged within the scope of the present invention to provide a single large opening including a filter means. Indeed, the portion of the hollow elongate member 15 between the rubber bung 19 and the second end 17 could be formed of a mesh-like material.

The present invention provides a medical irrigation device of relatively simple construction which can be made of glass, plastic or like material, and which can be produced at a cost to enable single use if desired. It is preferred that the reservoir is formed of clear material so that the withdrawn fluid can be readily observed.

Due to its construction, the device is readily disassembled into two or three parts; the reservoir 11, the hollow elongate member 15, and possibly the compressible bulb 12. This disassembly facilitates easy cleaning and sterilization of each of the individual parts. In addition, the ability to disassemble the device enables a selection of various elongate hollow members 15 having different pore sizes to be used. In practice, this feature enables an initial irrigation using an elongate hollow member having relatively large pores, and then, a subsequently irrigation using an elongate hollow member having a smaller pore size.

What is claimed is:

1. A medical irrigation device comprising a reservoir, a double-acting manually operable pump means, the reservoir having an inlet/outlet through which fluid may be displaced outwardly and inwardly by action of the pump means, a hollow member extending through the inlet/outlet the hollow elongate member having an open first end, positioned externally of the reservoir, adapted for connection to a resectoscope, and an open second end positioned within the reservoir, said second end being provided with a one-way valve means which allows fluid to pass into the reservoir, the hollow elongate member including a plurality of pores in the walls of portion of the hollow elongate member, said portion positioned within the reservoir and wherein said pores have a cross-sectional area substantially than the cross-sectional area of the second end of the hollow elongate member.

2. A medical irrigation device as claimed in claim 1 in which the inlet/outlet port is defined by an outwardly extending hollow projection.

3. A medical irrigation device claimed in claim 1 in which the elongate hollow member is releasably secured within the inlet/outlet port by means of a rubber bung provided on the hollow elongate member between the first and second ends.

4. A medical irrigation device as claimed in claim 1 in which the double-acting manually operable pump means is a compressible moiety connected to the reservoir.

5. A medical irrigation device as claimed in claim 4 in which the compressible moiety is a rubber bulb.

6. A medical irrigation device as claimed in claim 4 in which the compressible moiety is releasably connected to the reservoir via a short outwardly extending hollow projection.

7. A medical irrigation device as claimed in claim in which the double-acting manually operable pump means is provided by the reservoir being compressible.

8. A medical irrigation device as claimed in claim 1 in which the one-way valve means consists of a flap connected along one edge to the hollow elongate member by means of a hinge.

9. A medical irrigation device as claimed in claim 1 in which the pores have a cross-sectional area such as to prevent the passage of particulate matter into the elongate hollow member from the reservoir, and the second end of the elongate hollow member has a cross-sectional area such as to allow the passage of particulate matter from the elongate hollow member into the reservoir.

10. A medical irrigation device comprising a reservoir having first and second inlet/outlet ports, said first port being defined by a first outwardly extending hollow projection; a rubber bulb releasably connected to said reservoir via said port; said second port being defined by a second outwardly extending hollow projection; a hollow elongate member being releasably connected to the reservoir via said second port; said hollow elongated member having an open first end positioned externally of the reservoir, adapted for connection to a resectoscope, and an open second end positioned within the reservoir, said second end being provided with a gravity assisted, surge driven, flapper valve which allows fluid to pass into the reservoir, the hollow elongate member further including a plurality of pores in the walls of the portion of hollow elongate member positioned within the reservoir and the second outwardly extending hollow projection and which said pores have a cross-sectional area substantially smaller than the cross-sectional area of the second end of the hollow elongate member.

* * * * *

UNITED STATES PATENT AND TRADEMARK OFFICE
CERTIFICATE OF CORRECTION

PATENT NO. : 4,880,408

DATED : November 14, 1989

INVENTOR(S) : D.M. Cumes; T.C. Honikman

It is certified that error appears in the above-identified patent and that said Letters Patent is hereby corrected as shown below:

On the Front Page:

Abstract, line 2, change "ito" to -- into --.

Column 1, line 43, delete "is particularly".

Column 2, line 48, change "t he" to -- the --.
Column 2, line 66, after "reservoir" insert a period.

Column 5, lines 33,34, change "subsequently" to
-- subsequent --.

Column 5, lines 38-55, replace claim 1 in patent with correct version in application as follows:

-- 1. A medical irrigation device comprising a reservoir, a double-acting manually operable pump means, the reservoir having an inlet/outlet port through which fluid may be displaced outwardly and withdrawn inwardly by action of the pump means, a hollow elongate member extending through the inlet/outlet port, the hollow elongate member having an open first end, positioned externally of the reservoir, adapted for connection to a resectoscope, and an open second end positioned within the reservoir, said second end being provided with a one-way valve means which allows fluid to pass into the reservoir, the hollow elongate member

UNITED STATES PATENT AND TRADEMARK OFFICE
CERTIFICATE OF CORRECTION

PATENT NO. : 4,880,408

DATED : November 14, 1989

INVENTOR(S) : D.M. Cumes; T.C. Honikman

It is certified that error appears in the above-identified patent and that said Letters Patent is hereby corrected as shown below:

further including a plurality of pores in the walls of a portion of the hollow elongate member, said portion being positioned within the reservoir and wherein said pores have a cross-sectional area substantially smaller than the cross-sectional area of the second end of the hollow elongate member. --

Column 6, line 19, after "claim" insert -- 1 --.

Signed and Sealed this

First Day of October, 1991

Attest:

HARRY F. MANBECK, JR.

Attesting Officer   Commissioner of Patents and Trademarks